United States Patent
Hanessian et al.

[11] Patent Number: 6,025,487
[45] Date of Patent: Feb. 15, 2000

[54] ISOMERISATION PROCESS

[75] Inventors: Stephen Hanessian, Centreville, Canada; Michael John Rozema, North Chicago, Ill.

[73] Assignee: Glaxo Wellcome SpA, Verona, Italy

[21] Appl. No.: 09/000,211

[22] PCT Filed: Aug. 1, 1996

[86] PCT No.: PCT/EP96/03374

§ 371 Date: Mar. 27, 1998

§ 102(e) Date: Mar. 27, 1998

[87] PCT Pub. No.: WO97/06174

PCT Pub. Date: Feb. 20, 1997

[30] Foreign Application Priority Data

Aug. 5, 1995 [GB] United Kingdom .................. 9516118

[51] Int. Cl.$^7$ ................................................. C07D 205/08
[52] U.S. Cl. ........................................... 540/200; 540/302
[58] Field of Search ...................... 540/302, 200

[56] References Cited

FOREIGN PATENT DOCUMENTS

| 0 416 952 | 3/1991 | European Pat. Off. . |
| 0 422 596 | 4/1991 | European Pat. Off. . |
| 94 21637 | 9/1994 | WIPO . |
| 95 26333 | 10/1995 | WIPO . |

*Primary Examiner*—Mark L. Berch
*Attorney, Agent, or Firm*—Bacon & Thomas

[57] ABSTRACT

A process for the preparation of a compound (I)

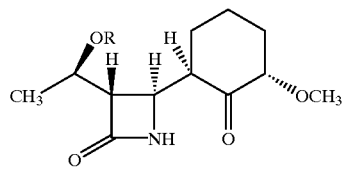

wherein R is a hydroxyl protecting group which comprises isomerising a compound of formula (I) wherein R is a hydroxyl protecting group by reacting the compound of formula (I) with a sterically hindered organic base in the presence of a Lewis acid and a compound of forumula (III)

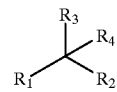

wherein $R_1$ and $R_2$ each independently represent cyano, $COR_5$ or $COR_2R_6$ or $R_1$ and $R_2$ together with the carbon atom to which they are attached from a C=O group;

$R_5$ represents alkyl, cycloalkyl, amino, alkylamino, dialkyl amino or optionally substituted phenyl or phenylalkyl group;

$R_6$ represents alkyl, cycloalkyl or optionally substituted phenyl or phenylalkyl group;

$R_3$ and $R_4$ represent each independently hydrogen, alkyl, alkoxy or optionally substituted phenyl group.

19 Claims, No Drawings

ISOMERISATION PROCESS

The present invention relates to a process for obtaining an intermediate useful in the preparation of antibacterial agents.

European Patent Application EP0416953 describes a novel class of tricyclic antibacterial agents and the process for their preparation. A particularly preferred compound described and claimed therein is the compound of formula (A)

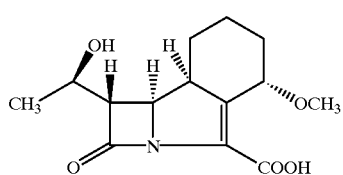

(A)

and salts thereof.

A key intermediate in the synthesis of compound of formula (A) is the azetidinone derivative of formula (I)

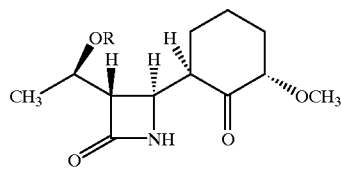

(I)

wherein R is a hydroxyl protecting group.

The process described therein for preparing the compound of formula (I) gives the compounds as a mixture of isomers from which it is separated. One of the other isomers that may be obtained by the general process described for preparation of compound of formula (I) is the compound of formula (II)

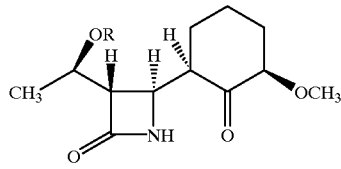

(II)

wherein R is a hydroxyl protecting group.

We have now found that it is possible to obtain a compound of formula (I) by isomerisation of the corresponding compounds of formula (II) in good yield without the need to use a chiral cyclohexanone derivative.

Thus the present invention provides a process for the preparation of a compound of formula (I) wherein R is a hydroxyl protecting group,

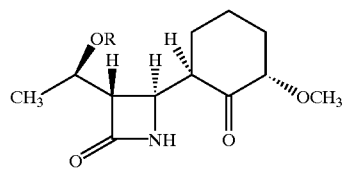

(I)

which comprises isomerisation of a compound of formula (II) wherein R is a hydroxyl protecting group by reaction in an aprotic solvent with a base in the presence of Lewis acid and a compound of formula (III).

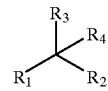

(III)

wherein
$R_1$ and $R_2$ each independently represent cyano, $COR_5$ or $CO_2R_6$ or $R_1$ and $R_2$ together with the carbon atom to which they are attached form a C=O group;
$R_5$ represents alkyl, cycloalkyl, amino, alkylamino, dialkyl amino or optionally substituted phenyl or phenylalkyl group;
$R_6$ represents alkyl, cycloalkyl or optionally substituted phenyl or phenylalkyl group;
$R_3$ and $R_4$ represent each independently hydrogen, alkyl, alkoxy or optionally substituted phenyl group.

The term alkyl as a group or part of a group when used herein refers to a straight or branched chain alkyl group containing from 1 to 4 carbon atoms. examples of such groups include methyl, propyl, isopropyl, n-butyl, isobutyl, secondary butyl or tertiary butyl.

The term cycloalkyl refers to a $C_{3-7}$ cycloalkyl group.

The term substituted phenyl or phenylalkyl refers to a group in which the phenyl moiety is substituted by 1 to 3 groups selected from halogen, alkyl, amino, alkylamino, dialkylamino, nitro, cyano.

Preferred compounds of formula (III) are those wherein $R_1$ and $R_2$ each independently represent cyano, $C_{1-4}$ alkoxycarbonyl eg. ethoxycarbonyl, methoxycarbonyl or t-butoxycarbonyl groups or those wherein $R_1$ and $R_2$ together with the carbon atom to which they are attached form a C=O group and $R_3$ and $R_4$ each independently represent hydrogen, phenyl or methyl group. Examples of such compounds include diethyl malonate, malononitrile, ethyl cyanoacetate, diethyl dimethylmalonate, diethyl methylmalonate di t-butylmalonate, benzaldehyde, benzophenene or t-butyl acetate.

Examples of suitable base for use in the reaction include sterically hindered organic bases for example lithium amides such as lithium diisopropyl amide, lithium bis (trimethylsilyl)amide or lithium tetramethyl piperidide.

Particularly convenient compounds of formula (III) are diethyl malonate, ethyl cyanoacetate or diethyl dimethyl malonate, di ter-butyl malonate or benzaldehyde of which diethyl malonate is particularly preferred.

Examples of suitable Lewis acid for use in the reaction include zinc salts such as zinc chloride or zinc bromide.

A particularly convenient Lewis acid for use in the reaction is zinc bromide.

The reaction is carried out in an aprotic solvent such as an ether e.g. tetrahydrofuran, a hydrocarbon such as hexane, cyclohexane or halohydrocarbon e.g chlorobenzene or mixtures thereof and preferably at a temperature within the range −78° to 10°.

The process of the invention may be carried out using a mixture of compound (II) and compound (I).

The hydroxyl protecting group R is preferably a trialkylsilyl group such as tri($C_{1-4}$)alkylsilyl group. Examples of suitable trialkylsilyl groups include trimethylsilyl and t-butyldimethylsilyl.

In a preferred embodiment of the invention the reaction is carried out using intermediate (II) or a mixture of intermediate (II) and, compound (I) wherein R is t-butyldimethylsilyl group with lithium diisopropyl amide in the presence of zinc bromide and diethyl malonate.

The intermediates of formula (II) or the mixture of intermediates (II) and compounds (I) are either known compounds or may be prepared by procedures described in EP 0416953. Alternatively they may be obtained by deallyloxycarbonylation reaction of compounds of formula (IV), wherein R has the meaning defined in formula (I)

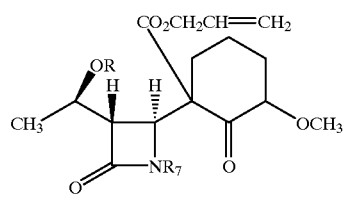

(IV)

and $R_7$ is a nitrogen protecting group followed by removal of N protecting group $R_7$.

The nitrogen protecting group $R_7$ is preferably a trialkylsilyl group such as tri($C_{1-4}$)alkylsilyl group. Examples of suitable trialkylsilyl groups include trimethylsilyl and t-butyldimethylsilyl. Particularly preferred is t-butyldimethylsilyl group.

The deallyloxycarbonylation reaction includes the removal of allyl group followed by decarboxylation reaction.

The allyl group may be removed by standard processes known for removing such a group.

Thus in one embodiment of this process the removal of allyl group may be carried out using palladium acetate and triphenyl phosphine and the decarboxylation may be carried out in the presence of organic acid such as formic acid.

The deallyloxycarbonylation reaction is preferably carried out in an aprotic solvent such as ethyl acetate at a temperature within the range 20–80°.

In the above reaction nitrogen protecting group may be removed by conventional procedures known for removing such groups. Thus for example compounds wherein $R_7$ is t-butyldimethylsilyl group may be deprotected by reaction with tetrabutylammonium fluoride and acetic acid. This process is conveniently carried out in a solvent such as tetrahydrofuran.

Compounds of formula (IV) may be prepared by reaction of azetidinone of formula (V)

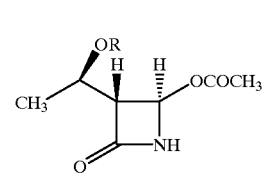

(V)

wherein R has the meaning defined in the formula (IV) with the enolate ion of the β ketoester (VI)

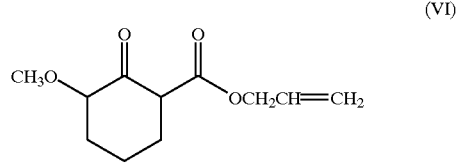

(VI)

followed by the conversion of the group NH into the nitrogen protected group $NR_7$ wherein $R_7$ has the meaning defined in the formula (IV).

The enolate ion of β ketoester (VI) is conveniently generated in situ by treatment with a suitable inorganic or organic base such as sodium hydride or lithium bis (trimethylsilyl)amide.

The reaction is carried out in an aprotic solvent such as ether e.g. tetrahydrofuran and at a temperature within the range −20° to +20° C.

The conversion of the group NH into the nitrogen protected group $NR_7$ may be obtained using conventional means for introducing such nitrogen protecting groups e.g. reaction with the group $R_7X$ wherein X is a leaving group e.g. halogen or methanesulphonate.

Thus the nitrogen protection reaction is carried out in an aprotic solvent such as dichloromethane with appropriate trialkylsilyl chloride or trialkylsilyl trifluoromethane sulphonate in the presence of tertiary organic base such as 2,6-dimethylpyridine.

Compound of formula (VI) may be prepared by reaction of compound of formula (VII)

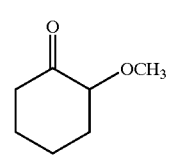

(VII)

with diallyl carbonate in a solvent such as an ether i.e tetrahydrofuran in the presence of a base such as sodium hydride, potassium hydride or a mixture thereof.

Compounds of formula (III) are either known compounds or may be prepared using methods described for analogous compounds.

The compound of formula (I) is a key intermediate in the synthesis of the antibacterial compound (A) and salts thereof and the process of the present invention has the advantage of providing the compound of formula (I) in good yield wihtout the need to use a chiral cyclohexanone derivative.

This invention also extends to the antibacterial compound of formula (A)

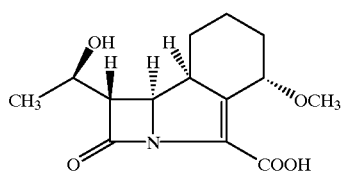

(A)

and salts thereof when prepared from a compound of formula(I) which has been obtained from compound of formula(II) according to the process of the invention.

The conversion of a compound of formula (I) of the invention into Compound A is specifically described in EP0416953, WO 94/21638 and WO 94/21637 and these specific processes are incorporated herein by reference.

In any of the above formulae A,(I),(II),(IV),(V), shown above the solid wedge shaped bond (◄■) indicates that the bond is above plane of the paper. The broken wedge shaped bond (▬▬▬▬) indicates that the bond is below plane of the paper.

In any of the formulae (IV), (VI) (VII) shown above when there is an asymmetric carbon atom and no specific configuration is shown then the formula includes all possible configurations.

In order that the invention may be more fully understood the following examples are given by way of illustration only.

In the Intermediates and Examples unless otherwise stated: chromatography was carried out over silica gel (Merck AG Darnstaadt, Germany).

All temperatures refer to ° C.

Proton Magnetic Resonance (1 H-NMR) was recorded at 300 or 400 Mhz as solutions in chloroform-d1 . Chemical shifts are reported in ppm downfield(delta) from Me4Si, used as internal standard, and are assigned as singolets (s), doublets(d), doublet of doublets (dd) or multiplets (m).

Solutions were dried over anhydrous magnesium sulfate.

Tc refers to thin layer chromatography on silica plates. The following abbreviations are used in the text: EA=ethyl acetate, CH=cyclohexane ,rt=room temperature.

INTERMEDIATE 1

Allyl 3-methoxy-2-oxocyclohexanecarboxylate

A slurry of 60% sodium hydride in mineral oil (2.4g) and 30% potassium hydride in mineral oil (50 mg) was washed three times with hexane (5 ml) and once with tetrahydrofuran (5 ml) and then suspended in tetrahydrofuran (20 ml) and diallyl carbonate (4.4 ml) This mixture was then brought to reflux and a tetrahydrofuran solution (5 ml) of 2-methoxycyclohexanone (2.5 ml) was added dropwise over 15 minutes. After refluxing for 12 hrs and cooling at room temperature, the reaction mixture was poured into a concentrated sodium hydrogen carbonate solution containing concentrated NH$_4$OH(2 ml) and was stirred at room temperature for 30 minutes. The aqueous layer was then acidified to pH 2 with concentrated hydrochloric acid and extracted three times with ether (100 ml). The combined organic layers were washed three times with saturated sodium hydrogen carbonate(50 ml), once with water (50 ml), once with brine (50 ml) and dried . After filtering and concentrating, the crude oil was purified by column chromatography eluting with hexane/ethyl acetate (4/1) , to afford the title compound as a mixture of tautomers and diastereomers (2.21 g)

$^1$H-NMR (300 MHz, CDCl3): 12.0(s), 6.02–5.85(m), 5.39–5.21(m), 4.82–4.76(m), 3.86–3.72(m), 3.52(s), 3.41 (s), 3.35(s), 2.4–1.9(m), 1.6–1.8 (m)

INTERMEDIATE 2

(3S,4R )-3-[(1R)-1-tert-butyidimethylsilyloxyethyl]-4-[(R)-2'-[(S)-6'-methoxy)-1'-oxocyclohexyl]] azetidin-2-one (2a) and (3S,4R)-3-[(1R)-1-tert-butyldimethylsilyloxyethyl]-4-[(R)-2'-[(R)-6'-methoxy)-1'-oxocyclohexyil]]azetidin-2-one(2b)

To a suspension of sodium hydride (60% in mineral oil, 750 mg) in tetrahydrofuran (20 ml) was added dropwise at –20° over 30 min. a tetrahydrofuran (10 ml) solution of intermediate 1 (1.34 g). After stirring at –20° for an additional 45 min., a tetrahydrofuran (30 ml) solution of (3S, 4R) 4-acetoxy-3-[(1 R)-1-tert-butyidimethylsilyloxyethyl]-azetin-2-one (1.72 g) was added dropwise at –20° over 30 min. After an additional 2 h. at –20°, the reaction was quenched by the addition of acetic acid (2 ml) and then was treated with a 10% solution of sodium hydrogen carbonate (50 ml) and extracted with ethyl acetate (300 ml). The organic layer was washed with brine, dried and evaporated affording the crude (3S ,4R)-3-[(1R)-1-tert-butyldimethylsilyloxyethyl]4-(2'-allyloxycarbonyl6'-methoxy -1 '-oxocyclohex-2-yl )azetidin-2-one product as a clear oil.

To a dichloromethane solution (20 ml) of the crude product prepared above cooled to 0° was added 2,6-dimethylpyridine (1.4 ml) and tert-butyldimethylsilyl trifluoromethanesulfonate (2.0 ml). After stirring for 30 min., the reaction was poured into water (50 ml) and the aqueous layer extracted three times with dichloromethane (100 ml). The combined organic layers were dried, filtered, and concentrated to give the crude (3S,4R)-1-tert-butyldimethylsilyl-3-[(1R)-1-tert-butyidimethylsilyioxyethyl]4-(2'-allyloxycarbonyl-6'-methoxy-1'-oxocyclohex-2-yl)azetidin-2-one product as a pale yellow oil.

Palladium acetate (13 mg) and triphenylphosphine (78 mg, 5 mol %) were suspended in ethyl acetate (15 ml) and formic acid (2.3 ml) was added. After refluxing this mixture for 30 min, an ethyl acetate (30 ml) solution of the crude N-TBS protected product, prepared above, was added dropwise over 30 min. After an additional reflux of 2.5 h., the reaction mixture was diluted with ethyl acetate (200 ml) and washed with saturated sodium hydrogen carbonate (50 ml) and brine (50 ml). After drying the organic phase, it was filtered through silica gel and concentrated to afford the crude (3S,4R)-1-tert-butyldimethylsilyl-3-[(1R)-1-tert-butyldimethylsilyloxyethyl]-4-(6'-methoxy-1'-oxocyclohex-2-yl)azetidin-2-one product as a pale yellow powder.

To a tetrahydrofuran (20 ml) solution of the above crude deallyloxycarbonylated product was added acetic acid (0.7 ml,) and a 1M tetrahydrofuran solution of tetrabutylammonium fluoride (9.0 ml). After stirring the reaction at room temperature for 15 min., it was then diluted with ethyl acetate (300 ml) and washed with sodium hydrogen carbonate (50 ml), water (50 ml), 10% solution of hydrochloric acid(50 ml), water(50 ml), brine(50 ml), and dried. The organic layer was filtered, concentrated, and purified by flash chromatography (CH/EA, 4:1 to 0:1) to afford three fractions.

2a isomer(600 mg) and 2b isomer (870 mg).

The third fraction (235 mg) gave (3S,4R)-3-[(1R)-1-tert-butyidimethylsilyloxyethyl]-4-[(S)-2'-[(S)-6'-methoxy)-1'-oxocyclohexyl]]azetidin-2-one

INTERMEDIATE 2a mp: 127–129°

$^1$H-NMR (300 MHz, CDCl3): 5.76 (s, 1H) 4.24–4.15 (m, 1H), 4.02–4.00 (m, 1H), 3.58 (apparent t, 1H), 3.29 (s, 3H), 3.10(1H J), 2.89 (dd, 1H, J), 2.28–2.21 (m, 1H), 2.15–1.96 (m, 2H), 1.73–1.52 (m, 3H), 1.26 (d, 3H), 0.88 (s, 9H), 0.09 (s, 3H) 0.08 (s, 3H)

INTERMEDIATE 2b mp 129–131°

$^1$H-NMR (300 MHz, CDCl3): 5.76(s), 4.23–4.12(m), 4.09(t), 3.81(dd), 3.46(s), 2.62–2.54(m), 2.47–2.40, 2.16–1.99(m), 1.81–1.57(m),1.25(d), 0.88(s), 0.09(s), 0.07 (s)

EXAMPLE 1

(3S,4R)-3-[(1R)-1-tert-butyldimethylsilyloxyethyl]-4-[(R)-2'-[(S)-6'-methoxy)-1'-oxocyclohexyl]azetidin-2-one Method A To a solution of Lithium diisopropylamide, prepared by adding butyllithium (3.4 ml, 2.5 M in hexane) to a tetrahydrofuran solution of diisopropylamine (1.3 ml) at 0° and stirring for 15 min., cooled to −78° was added dropwise a tetrahydrofuran (10 ml) solution of Intermediate 2 as a mixture of 2a and 2b isomers (1:1)(1.0 g) over 15 min. After an additional 30 min. a tetrahydrofuran solution of zinc bromide (prepared by refluxing a tetrahydrofuran (10 ml) solution of 1,2-dibromoethane (0.26 ml) over zinc powder (390 mg) for 2 h.) was added via cannula and the reaction was allowed to warm to −10° over 30 min. The reaction mixture was then cooled to −78°, a tetrahydrofuran (5 ml) solution of diethyl malonate was added . The reaction was warmed to room temperature over 30 min., then poured into saturated aqueous solution of ammonium chloride (50 ml) and extracted two times with ethyl acetate (100 ml). The aqueous phase was made acidic by the addition of 10% hydrocloric acid (10 ml) and extracted with additional ethyl acetate (100 ml). The combined organic layers were washed with brine (50 ml) and dried . Filtration, removal of the solvents on the rotoevaporator, and flash chromatography (CH/EA, 2:1) afforded 766 mg of title compound as a crystalline solid mp.:127–129°

[a]$_0$31.9° (c 1.06, CHCl$_3$)

IR (CHCl$_3$):3440 (NH), 2950, 2870, 1770 β-Lactam CO), 1740 (cHex CO), 1520, 1100 cm$^1$ $^1$H-NMR (300 MHz, CDCl3): 5.76 (s, 1H) 4.24–4.15 (m, 1H), 4.02–4.00 (m, 1H), 3.58 (apparent t, 1H), 3.29 (s, 3H), 3.10(1H J), 2.89 (dd, 1H, J), 2.28–2.21 (m, 1H), 2.15–1.96 (m, 2H), 1.73–1.52 (m, 3H) 1.26 (d, 3H), 0.88 (s, 9H) 0.09 (s, 3H), 0.08 (s, 3H)

The required product of Example 1 was also obtained using the procedure described in Method A above but wherein the diethyl malonate was replaced by one of the following compounds:

(i) ethyl cyanoacetate
(ii) diethyl methylmalonate
(iii) diethyl dimethyl malonate
(iv) benzaldehyde Method B To a solution of Lithium diisopropylamide[prepared by adding butyllithium (10.5 ml, 16.9 mmol, 1.6M in hexanes) to a tetrahydrofuran (18 ml) solution of diisopropylamine (2.4 ml,) at −10÷0° C. and stirring for 20 min.] at −10÷0° C. was added dropwise a tetrahydrofuran (20 ml) solution of (3S,4R)-3-[(1R)-1-tert-butyldimethylsilyloxyethyl]-4-[(R)-2'-[(R')-6'-methoxy)-1'-oxocyclohexyl]]azetidin-2-one (2 g) over 20 min. After additional 30 min, a tetrahydrofuran (15 ml) solution of zinc bromide (2.7 g) was added dropwise over 5 min. The stirring at −10÷0° C. was extended for 30 min., then a tetrahydrofuran (3 ml) solution of diethyl malonate (2.5 ml) was added and the reaction was allowed to warm to room temperature. The reaction mixture was then poured into saturated aqueous solution of ammonium chloride (100 ml) and extracted with ethyl acetate (2×150 ml). The aqueous phase was made acidic by the addition of 10% solution of hydrochloric acid (30 ml) and extracted with ethyl acetate (1×100 ml). The combined organic layers were washed with brine (1×200 ml) and dried over Na$_2$SO$_4$. Filtration, removal of the solvents under vacuum, and flash chromatography (Cy/EtOAc, 3/2) afforded the title compound(1.38 g).

$^1$H-NMR (500 MHz, CDCl$_3$): 5.76 (bs, 1H), 4.18 (m, 1H), 3.99 (m,1H), 3.58 (m, 1H), 3.28 (s, 3H), 3.09 (m, 1H), 2.88 (dd, 1H), 2.25 (m,1H), 2.2–1.95 (m, 2H), 1.8–1.52 (m, 3H), 1.26 (d, 3H), 0.88 (s, 9H), 0.087 (s, H), 0.07 (s, 3H).

The product of Example 1 was also obtained using the procedure described in Method A above but wherein the lithium diisopropylamide was replaced by lithium bis (trimethylsilyl)amide or lithium tetramethyl piperidide.

We claim:

1. A process for the preparation of a compound wherein R is a hydroxyl protecting group

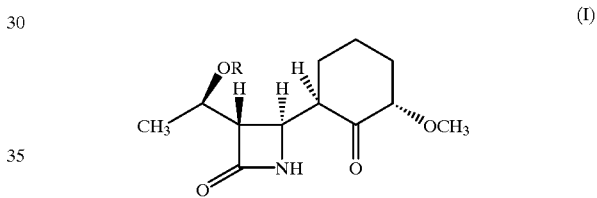

(I)

which comprises isomerisation of a compound of formula (II) wherein R is a hydroxyl protecting group

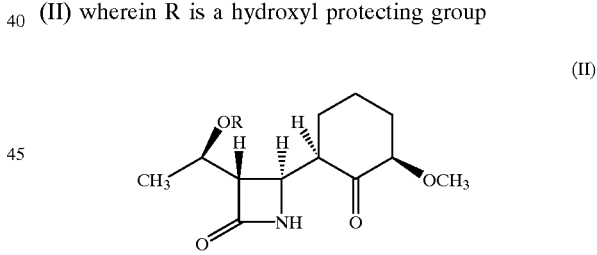

(II)

by reaction in an aprotic solvent with a sterically hindered organic base in the presence of a Lewis acid and a compound of formula (III)

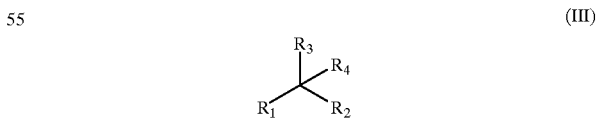

(III)

wherein

R$_1$ and R$_2$ each independently represent cyano, COR$_5$ or CO$_2$R$_6$ or R$_1$ and R$_2$ together with the carbon atom to which they are attached form a C=O group;

R$_5$ represents alkyl, cycloalkyl, amino, alkylamino, dialkyl amino or optionally substituted phenyl or phenylalkyl group;

$R_6$ represents alkyl, cycloalkyl or optionally substituted phenyl or phenylalkyl group;

$R_3$ and $R_4$ represent each independently hydrogen, alkyl, alkoxy or optionally substituted phenyl group, in an aprotic solvent.

2. A process as claimed in claim 1 wherein the compound of formula (III) is a compound wherein $R_1$ and $R_2$ each independently represent cyano, $COR_5$ or $CO_2R_6$, and $R_3$ and $R_4$ each independently represent hydrogen alkyl or optionally substituted phenyl.

3. A process as claimed in claim 1 wherein the base is selected from a lithium diisopropyl amide, lithium bis(trimethylsilyl)amide or lithium tetramethyl piperidide.

4. A process as claimed in claim 1 wherein the Lewis acid is zinc bromide.

5. A process as claimed in claim 1 wherein the compound of formula (III) is selected from diethyl malonate, ethyl cyanoacetate, diethyl dimethyl malonate, diethyl methyl malonate or benzaldehyde.

6. A process as claimed in claim 1 wherein the compound of formula (III) is diethyl malonate.

7. A process as claimed in claim 1 wherein the hydroxyl protecting group R is a t-butyidimethylsilyl group.

8. A process as claimed in claim 1 wherein the reaction is carried out at a temperature within the range −78° to 0° C.

9. A process as claimed in claim 6 wherein the hydroxyl protecting group R is a t-butyidimethylsilyl group.

10. A process as claimed in claim 3 wherein the reaction is carried out at a temperature within the range of −78° to 0° C.

11. A process as claimed in claim 3 wherein the Lewis acid is zinc bromide.

12. A process as claimed in claim 3 wherein the compound of formula (III) is selected from diethyl malonate, ethyl cyanoacetate, diethyl dmethyl malonate, diethyl methyl malonate or benzaldehyde.

13. A process as claimed in claim 4 wherein the compound of formula (III) is selected from diethyl malonate, ethyl cyanoacetate, diethyl dmethyl malonate, diethyl methyl malonate or benzaldehyde.

14. A process as claimed in claim 3 wherein the compound of formula (III) is diethyl malonate.

15. A process as claimed in claim 4 wherein the compound of formula (III) is diethyl malonate.

16. A process as claimed in claim 5 wherein the compound of formula (III) is diethyl malonate.

17. A process as claimed in claim 3 wherein the hydroxyl protecting group R is a t-butyidimethylsilyl group.

18. A process as claimed in claim 4 wherein the hydroxyl protecting group R is a t-butyldimethylsilyl group.

19. A process as claimed in claim 5 wherein the hydroxyl protecting group R is a t-butyldimethylsilyl group.

* * * * *